United States Patent [19]

Kieczykowski

[11] Patent Number: 5,019,651
[45] Date of Patent: May 28, 1991

[54] PROCESS FOR PREPARING 4-AMINO-1-HYDROXYBUTYLIDENE-1,1-BISPHOSPHONIC ACID (ABP) OR SALTS THEREOF

[75] Inventor: Gerard R. Kieczykowski, Westfield, N.J.

[73] Assignee: Merck & Co., Inc., Rahway, N.J.

[21] Appl. No.: 540,997

[22] Filed: Jun. 20, 1990

[51] Int. Cl.$^5$ .............................................. C07F 9/38
[52] U.S. Cl. ........................................................ 562/13
[58] Field of Search .......................................... 562/13

[56] References Cited

U.S. PATENT DOCUMENTS

| | | | |
|---|---|---|---|
| 3,848,420 | 11/1974 | Wollman et al. | 562/13 |
| 4,054,598 | 10/1977 | Blum et al. | 562/13 |
| 4,064,164 | 12/1977 | Blum et al. | 562/13 |
| 4,100,167 | 7/1978 | Radhakrishnan et al. | 562/13 |
| 4,157,364 | 6/1979 | Buckman et al. | 562/13 |
| 4,267,108 | 5/1981 | Blum et al. | 562/13 |
| 4,304,734 | 12/1981 | Jary et al. | 260/502.5 |
| 4,327,039 | 4/1982 | Blum et al. | 562/13 |
| 4,407,761 | 10/1983 | Blum et al. | 562/13 |
| 4,418,019 | 11/1983 | Klose et al. | 562/13 |
| 4,578,376 | 3/1986 | Rosini | 514/108 |
| 4,621,077 | 11/1986 | Rosini et al. | 514/108 |
| 4,624,947 | 11/1986 | Blum et al. | 562/13 |
| 4,705,651 | 11/1987 | Staibano | 562/13 |
| 4,711,880 | 12/1987 | Stahl et al. | 562/13 |
| 4,814,326 | 3/1989 | Rosini et al. | 562/13 |
| 4,922,007 | 5/1990 | Kieczykowski et al. | 562/13 |

OTHER PUBLICATIONS

Bulletin of Academy of Sciences of the U.S.S.R., Band 27, No. 2, Teil 2 (1978).
Lancet, Apr. 14, 1979, pp. 803–805.

*Primary Examiner*—J. E. Evans
*Attorney, Agent, or Firm*—Robert J. North; Charles M. Caruso

[57] ABSTRACT

An improved process is described for the preparation of 4-amino-1-hydroxybutylidene-1,1-bisophosphonic acid (ABP) or salts thereof which comprises:

(a) reacting 4-aminobutyric acid with a mixture of phosphorous acid and $PCl_3$ in the presence of methanesulfonic acid;

(b) contacting the mixture from Step (a) with an aqueous hydrolysis mixture, wherein the pH is maintained in the range of 4 to 10 during the contacting; and (c) recovering said 4-amino-1-hydroxybutylidene-1,1-bisphosphonic acid or salts thereof.

10 Claims, No Drawings

PROCESS FOR PREPARING 4-AMINO-1-HYDROXYBUTYLIDENE-1,1-BIS-PHOSPHONIC ACID (ABP) OR SALTS THEREOF

BACKGROUND OF THE INVENTION

This invention relates to an improved process for making 4-amino-1-hydroxybutylidene-1,1-bisphosphonic acid (ABP) or salts thereof, where the end product is obtained in pure form and high yield, and which avoids the use of a strongly-acidic hydrolysis medium.

It is known according to U.S. Pat. No. 4,407,761 to Henkel Kommanditgesellschaft to prepare 4-amino-1-hydroxy-butylidene-1,1-bisphosphonic acid by bisphosphonating an aminocarboxylic acid with phosphonating reactants and then quenching the reaction mixture by addition of a strong non-oxidizing acid, preferably concentrated hydrochloric acid, with heating, to hydrolyze the formed phosphorous intermediates to final product. However, problems result from this reaction because the bisphosphonation reaction mixture does not remain homogeneous and local solidification occurs. This solidification causes variable yields, which in part results from the exothermic nature of the reaction due to the development of "hot spots". Moreover, to make the sodium salt, utilizing the prior art processes, requires isolation of 4-amino-1-hydroxybutylidene-1,1-bisphosphonic acid and an additional step to convert this to the monosodium salt. Further, the use of concentrated hydrochloric acid in the quench, whose fumes present an environmental problem, is also required.

Furthermore, U.S. Pat. No. 4,922,007 to G. R. Kieczykowski, et al. (assigned to Merck & Co., Inc.) discloses the use of methanesulfonic acid to overcome the non-homogeneity and solidification problems associated with the bisphosphonation phase, but utilizes a non-pH controlled water quench which leads to the presence of a strongly acidic and corrosive hydrolysis mixture which requires the use of expensive glass reaction vessels with their inherent pressure limitations.

The present invention solves these problems by the use of methanesulfonic acid to allow the bisphosphonation reaction to remain fluid and homogeneous, and using a pH-controlled aqueous quench in the range of 4 to 10, followed by hydrolysis, which eliminates the need for concentrated hydrochloric acid in the quench. The present invention also eliminates the need to handle a corrosive acidic product hydrolysis mixture, such that stainless steel hydrolysis equipment rather than glass equipment can be utilized. Glass equipment has inherent pressure limitations not possessed by stainless steel. This is a big advantage in the instant process since it has been found that, by conducting the hydrolysis under pressure, the hydrolysis rate can be significantly increased.

It has been found that, in the quench, a pH above 10 leads to lower yields due to formed intermediates which resist hydrolysis, and a pH below 4 leads to much longer hydrolysis times. Further, it has been found that ABP is unstable at a pH above 8, thus limiting the reaction times and hydrolysis times at higher pHs.

SUMMARY OF THE INVENTION

By this invention, there is provided a process for the preparation of 4-amino-1-hydroxy-butylidene-1,1-bisphosphonic acid or salts thereof which comprises:

(a) reacting 4-aminobutyric acid with a mixture of phosphorous acid and $PCl_3$ in the presence of methanesulfonic acid;

(b) contacting the resulting mixture from Step (a) with an aqueous hydrolysis mixture, wherein the pH is maintained in the range of 4 to 10 during the contacting; and (c) recovering said 4-amino-1-hydroxybutyl-idene-1,1-bisphosphonic acid or salts thereof.

The reaction can further be conducted by controlling the pH during the aqueous quench in a narrow range, i.e. 6–8, maintaining the temperature between 0°-20° C., and then heating the hydrolysis mixture at 50° C. - reflux, or under pressure for a sufficient time to insure complete hydrolysis to the titled product.

DETAILED DESCRIPTION OF THE INVENTION

The present invention process provides pure crystallized 4-amino-1-hydroxybutylidene-1,1-bisphosphonic acid, or salts thereof, which can surprisingly be obtained in high yields. The invention involves the bisphosphonation of an aminoalkane carboxylic acid with phosphonating reactants in the presence of methanesulfonic acid, quenching the reaction mixture with an aqueous hydrolysis mixture, maintaining the pH at 4 to 10, hydrolyzing the phosphorus intermediates, formed in the quench procedure, and recovering 4-amino-1-hydroxybutylidene-1,1-bisphosphonic acid or salts thereof. The compound can be crystallized directly from the reaction mixture in about 90% yield after the pH controlled hydrolysis, and pH adjustment to about 4.3 with no further purification necessary.

The aminoalkane carboxylic acids which can be used is 4-aminobutyric acid. The bisphosphonation reaction generally takes place at temperatures of from 45° to 125° C., preferably at about 65° C.

Generally 1 to 3, preferably 2.0 moles of $H_3PO_3$ and generally 1 to 5.0, preferably 4.0 mols of $PCl_3$ are used per mol of aminocarboxylic acid. Smaller amounts of 4-aminobutyric acid can be used which limits the formation of ABP dimers and decreases the necessary hydrolysis times. If desired, inert organic diluents, which do not solubilize the reaction product, particularly helped or chlorinated hydrocarbons, such as chlorobenzene, tetrachloroethane, tetrachloroethylene and trichloroethylene can be used in the reaction with methanesulfonic acid.

Following the reaction to form the product, the reaction is quenched, i.e. drowned into an aqueous hydrolysis mixture. The conditions of the quench are such that pH is controlled in the range of pH 4 to 10, and preferably the pH is controlled in a narrow pH region, i.e. 6–8. By controlling the pH in this manner, it has been found that the yield of ABP can be maximized.

The aqueous hydrolysis mixture can contain basic or acidic materials or buffering agents.

Representative examples include sodium, potassium and lithium hydroxides, carbonates, bicarbonates, dihydrogen phosphates, hydrogen phosphates, borates, oxalates, tartrates, phthalates, phosphorous acid salts, and the like, and mixtures thereof.

Preferred is where the hydrolysis mixture is a buffered solution, preferrably a phosphate or bicarbonate buffered solution in the range pH 6–8.

The pH of the resulting quench mixture can also be controlled during the hydrolysis drown by the simultaneous addition of a basic reagent, e.g. sodium hydroxide.

The temperature of the quench is carried out in the range of 0°-90° C., and preferably 0°-20° C.

The required time of the quench drowning procedure will vary according to the volumes used.

Following the pH-controlled, temperature-controlled quench, the resulting mixture is stirred and heated in the temperature range of 50° C. to reflux and preferably at the reflux temperature of about 105°-110° C. to complete and insure complete hydrolysis.

The volume ratio of the reaction mixture from the phosphonation Step (a) to the volume of the aqueous hydrolysis mixture in the quench Step (b) is about 1 to 5.

Alternatively, the hydrolysis mixture can be partially concentrated to about half the original volume, by distillation at atmospheric or reduced pressure, diluted with water to about the original volume and then refluxed. This procedure substantially reduces the hydrolysis time.

As a further alternative, the hydrolysis mixture can be heated at 110°-165° C. in a closed vessel under pressure. This also substantially reduces the hydrolysis times.

It should be noted that a pH above about 7-8, the product ABP starts to undergo degradation with resultant yield loss, and thus preferably the desired hydrolysis workup procedure should be carried out in the pH range 6-8.

The reaction is schematically represented as follows:

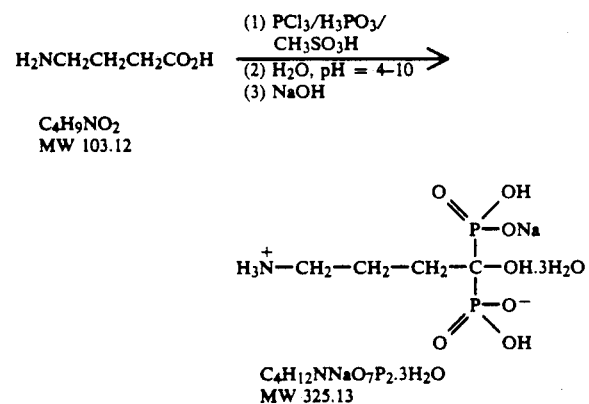

4-amino-1-hydroxybutylidene-1,1-bisphosphonic acid monosodium salt trihydrate described here is useful as a pharmaceutical composition and for the treatment or prevention of diseases involving bone resorption. Such diseases as hypercalcemia of malignancy, Paget's disease, and osteoporosis are advantageously treated with 4-amino-1-hydroxybutylidene-1,1-bisphosphonic acid monosodium salt trihydrate made according to the process of the present invention.

Other pharmaceutically acceptable salts, such as for example the calcium, potassium salts, can be prepared according to the processes of the present invention and are included within the scope thereof.

The following examples are illustrative of the practice of the invention without being limiting in any way.

EXAMPLE 1

Non-pH-Controlled Hydrolysis

Preparation of 4-amino-1-hydroxybutylidene-1,1-bisphosphonic acid monosodium salt trihydrate Bisphosphonation Reaction Phase A 250 mL flask was fitted with a mechanical stirrer, a thermocouple, an addition funnel and a reflux condenser through which is circulated −20° C. brine. The system was connected to a caustic scrubber which places a back pressure of 0.5-1 psig on the system. The system was flushed with nitrogen and charged with 20 g (0.19 mol) of aminobutyric acid, 80 mL of methanesulfonic acid, and 24 g (0.29 mol) of phosphorous acid. For larger scale operations, the methanesulfonic acid can be charged first, followed by the 4-aminobutyric acid and phosphorous acid. Upon mixing, the heat of neutralization and solution increased the reaction temperature to 75° C. The suspension was aged for 15 minutes at 70°-75° C. resulting in a clear colorless solution. The solution was cooled to 35° C. and phosphorus trichloride ($PCl_3$), 40 mL (0.46 mol) was added cautiously over 20 minutes. The reaction was then heated to 65° C. and aged at that temperature for 20 hours. The reaction should not be allowed to get much above 65° C. The reaction becomes self-heating above 85° C. and under adiabatic conditions the temperature will increase steadily. At about 150 degrees an exotherm accompanied by a large pressure release occurs. It is therefore recommended that the reaction be immediately quenched into cold water if the temperature reaches 85° C.

Quench; Hydrolysis

The reaction was then cooled to 25° C. and added to 200 mL of deionized water over 5 minutes. The flask was rinsed with an additional 100 mL of water and the combined strongly-acid solution (pH less than zero) aged at 95°-100° C. for 5 hours. The reaction was cooled to 20° C. and maintained at 20°-25° C. while the pH was adjusted to 4.3 with ca. 80 mL of 50% NaOH. The resulting white suspension was then cooled to 0°-5° C. and aged for 1 hour. The pH was readjusted to 4.3 if necessary and the suspension aged at 0°-5° C. for an additional 2 hours. The product was collected by filtration, then washed with 2×50 mL of cold (0°-5° C.) water and 100 mL of 95% EtOH. The yield after air drying at 40° C. to constant weight was 56.4 g (90%).

EXAMPLE 2

Use of pH-Controlled Hydrolysis 4-aminobutyric acid: 20 g
methanesulfonic acid: 160 ml
phosphorous acid: 32 g
phosphorus trichloride: 80 ml Bisphosphonation Reaction Phase The above reagents were mixed and heated at 65° C. for 5 hours analogously according to the procedure of Example 1.

Quench; Hydrolysis

The reaction mixture was quenched over 35 minutes by adding dropwise to a solution of 10 g $Na_2HPO_4$ in one liter of water, at pH=7.0. The pH of the quench was maintained between 6.0 and 7.0 by simultaneously adding 25% sodium hydroxide and maintained below 25° C. by cooling with ice. Once the quench was complete, the pH was adjusted to 7.0 and the solution concentrated to 1080 ml by atmospheric distillation (100°-104° C.) over 3 hours. At this point, the reaction was subdivided into 2 parts, A and B.

A, being 630 ml, was concentrated further to 450 ml after adjusting the pH to 4.3. The solution was aged overnight at ambient temperature during which time the product crystallized. The suspension was aged at 0° C. for 2 hours then filtered, washed with 100 ml of cold water, 100 ml of 1:1 water/ethanol, and 100 ml of 100% ethanol and dried, yielding 20.5 g (56% yield).

B, being 450 ml, was treated by refluxing an additional 16 hours before adjusting the pH to 4.3 and concentrating to 300 ml. The product was isolated as above providing 16.5 g. (63% yield) of ABP.

This Example illustrates that the above bisphosphonation reaction, in conjunction with a buffered quench, minimized the ABP dimers and phosphonates which are more difficult to hydrolyze, thus reducing the required hydrolysis times.

EXAMPLE 3

4-aminobutyric acid: 60 g
methanesulfonic acid: 240 ml
phosphorous acid: 48 g
phosphorus trichloride: 120 ml Bisphosphonation The reaction was run analogously using the procedure described in Example 1 (65° C. overnight) with the above quantity of reagents. The total reaction volume was 430 ml. The reaction was subdivided into aliquots prior to quenching.

Quench; Hydrolysis

Aliquots were quenched into 100 ml of water while simultaneously adding 20% sodium hydroxide to maintain a pH of 6–10. The pH was adjusted to different values between 4–10 and the reaction refluxed for an appropriate amount of time to produce and isolate product (see below). The pH was then adjusted to 7 and the solution filtered. The pH was then adjusted to 4.3 and the solution aged overnight during which time the product crystallized. The suspension was then aged at 0° C. for 2 hours and filtered. The cake was washed with water then ethanol and dried.

| Aliquot | pH | Time Refluxed[1] | Yield |
|---------|----|----|----|
| 50 ml | 11 | 1 day | 9.6 g (44%) |
| 46 ml | 10 | 2 days | 11.4 g (56%) |
| 20 ml | 9 | 2 days | 5.0 g (54%) |
| 23 ml | 8 | 6 days | 6.8 g (66%) |
| 21 ml | 7 | 10 days | 6.6 g (72%) |
| 21 ml | 7 | 10 days | 7.2 g (78%)[2] |
| 21 ml | 7 | 5 days | 7.0 g (75%)[3] |
| 21 ml | 7 | 42 hrs.[4] | 2.4 g (65%) |
| 21 ml | 6 | 11 days | 6.8 g (74%) |
| ml | 5 | days[5] | g ( %) |
| ml | 4 | days[5] | g ( %) |
| ml | 3 | days[5] | g ( %) |

[1] Temperature between 105-110° C. at 1 atmosphere.
[2] Used an equal volume of ethanol in the crystallization.
[3] Partially concentrated by atmospheric distillation to about half the volume, diluted with an equal volume of water and then refluxed.
[4] After quenching, refluxed at 140° C. in a closed pressure vessel.
[5] After 12 days, the hydrolysis mixture was analyzed by phosphorus NMR. The pH = 5 and pH = 4 reactions indicated incomplete hydrolysis mixtures. The pH = 3 reaction indicated incomplete hydrolysis mixture and significantly longer hydrolysis times projected for its completion.

This Example illustrates that the product can be quenched and hydrolyzed under neutral and basic conditions in good yield, but that at the higher pH values, the yields are lower due to competing degradation of the product.

What is claimed is:

1. A process for the preparation of 4-amino-1-hydroxybutylidene-1,1-bisphosphonic acid or salts thereof which comprises:
   (a) reacting 4-aminobutyric acid with a mixture of phosphorous acid and $PCl_3$ in the presence of methanesulfonic acid;
   (b) contacting the resulting mixture from Step (a) with an aqueous hydrolysis mixture, wherein the pH is maintained the range at 4 to 10 during the contacting; and
   (c) recovering said 4-amino-1-hydroxybutylidene-1,1-bisphosphonic acid or salts thereof.

2. The process of claim 1 wherein the pH is maintained in Step (b) in the range of 6–8.

3. The process of claim 1 further comprising step (b-2), heating said resulting mixture from Step (b) in the range of 50° C. to the boiling point.

4. The process of claim 1 wherein said Step (b) is conducted at a temperature of from 0° C. to 90° C.

5. The process of claim 4 wherein said temperature is 0°-20° C.

6. The process of claim 1 wherein said aqueous hydrolysis mixture in Step (b) is a phosphate buffer.

7. The process of claim 6 wherein said buffer comprises monosodium dihydrogen phosphate and disodium monohydrogen phosphate.

8. The process of claim 1 wherein 4-amino-1-hydroxybutylidene-1,1-bisphosphonic acid monosodium salt trihydrate is recovered.

9. The process of claim 1 wherein 4-amino-1-hydroxybutylidene-1,1-bisphosphonic acid is recovered.

10. A process for the preparation of 4-amino-1-hydroxybutylidene-1,1-bisphosphonic acid or salts thereof which comprises:
   (a) reacting 4-aminobutyric acid with a mixture of phosphorous acid and $PCl_3$ in the presence of methanesulfonic acid at a temperature of about 65° C.;
   (b) contacting the resulting mixture from Step (a) with an aqueous phosphate buffer at a temperature in the range of 0°-20° C., and maintaining the pH between 6–8 during the contacting;
   (b-2) heating the resulting mixture from Step (b) at the boiling point; and
   (c) recovering said 4-amino-1-hydroxybutylidene-1,1-bisphosphonic acid or salts thereof.

* * * * *